Figure 1:
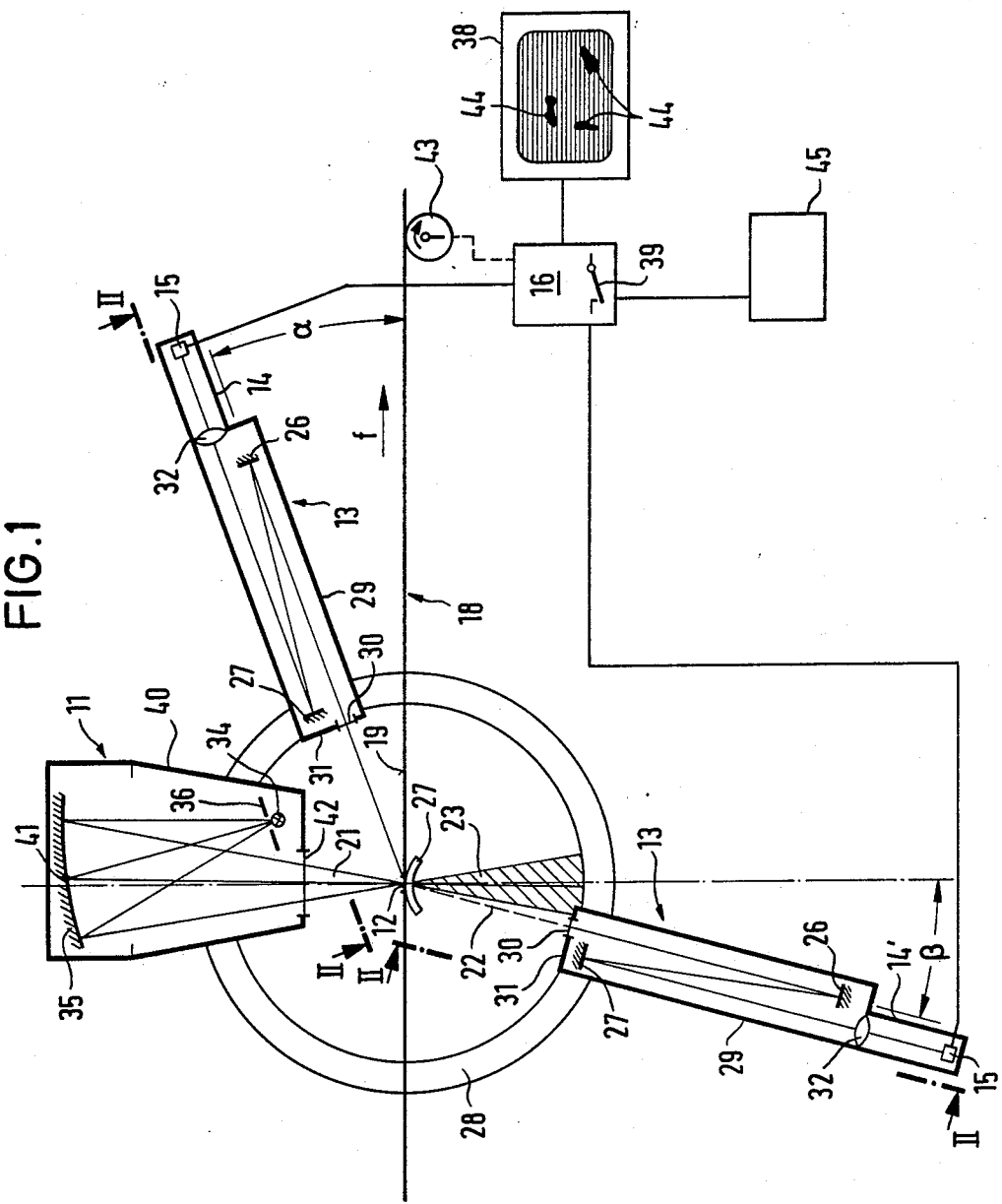

United States Patent [19]

Weber et al.

[11] Patent Number: 4,900,153
[45] Date of Patent: Feb. 13, 1990

[54] OPTICAL SURFACE INSPECTION APPARATUS

[75] Inventors: Klaus Weber, Königsbronn; Klaus Ostertag, München, both of Fed. Rep. of Germany

[73] Assignee: Erwin Sick GmbH Optik-Elektronik, Waldkirch, Fed. Rep. of Germany

[21] Appl. No.: 254,331

[22] Filed: Oct. 6, 1988

[30] Foreign Application Priority Data

Oct. 9, 1987 [DE] Fed. Rep. of Germany ....... 3734294

[51] Int. Cl.$^4$ ............................................. G01N 21/89
[52] U.S. Cl. ................................... 356/430; 250/562; 356/238
[58] Field of Search .................. 356/429, 430, 238; 250/562, 572

[56] References Cited

U.S. PATENT DOCUMENTS

| | | | |
|---|---|---|---|
| 3,841,761 | 10/1974 | Selgin | 250/562 X |
| 4,099,884 | 7/1978 | Nash | 356/430 |
| 4,671,663 | 6/1987 | Sick | 356/430 |

Primary Examiner—Davis L. Willis
Assistant Examiner—Matthew W. Koren
Attorney, Agent, or Firm—Townsend and Townsend

[57] ABSTRACT

An optical surface inspection apparatus for material webs comprises an illuminating means (11) for generating a strip of light (12) on the surface (19) to be inspected and a light receiving means (13) which receives the light emitted (diffusely reflected) from the surface region illuminating by the strip of light (12) and directs it to a photoreceiving arrangement, which delivers a signal representative of web faults to an electronic processing circuit (16). The light receiving means (13) has at least one row camera (14) which receives light remitted from a line illuminated by the strip of light (12) and forms an image of the line on the diode row (15). The light receiving means is also arranged at such a shallow observing angle α relative to the tangential plane to the surface at the location of the strip of light (12) that faults (20) which project slightly out of the surface appear to the row camera (14) in shadow outline against the light background of the strip of light (12).

19 Claims, 3 Drawing Sheets

OPTICAL SURFACE INSPECTION APPARATUS

The invention relates to an optical surface inspection apparatus for material webs the apparatus comprising an illuminating means for generating a strip of light on the surface of the material web to be inspected and a photoelectric light receiving means which receives the light remitted or diffusely reflected from the surface region illuminated by the strip of light and which directs it to a photoreceiving arrangement, with the photoreceiving arrangement delivering a signal representative of web faults to an electronic processing circuit.

Laser scanners are generally used for the automatic surface inspection of textile material webs with the laser scanners scanning a material web moving over a deflection roller transverse to its direction of movement in order to seek surface faults to distinguish them and to register them. The invention is in particular concerned with woven textile materials in which the fault recognition is particularly problematic.

The object of the present invention is to provide and optical surface inspection apparatus for material webs of the initially named kind, with it being possible to renounce the use of a laser as a light source and of a rapidly rotating mirror wheel, but with the apparatus being able to find and discriminate at least the most disturbing faults which occur in textile production. In order to make the discrimination of the faults possible the various faults must also provide signals and signal combinations which differ as distinctly as possible.

In order to satisfy this object there is provided an apparatus of the initially named kind which is characterized in that the light receiving device includes at least one row camera having a diode row and serving as a photoreceiving arrangement, with the row camera receiving remitted light from a line on the surface which is illuminated by the light strip and forming an image of the line on the diode row, and with the row camera also being arranged at such a shallow observing angle $\alpha$ to the tangential plane to the surface at the location of the light strip that faults of low height which project out of the surface of the material web appear to the row camera as a shadow outline against the bright background of the light strip, so that a corresponding electrical signal is transmitted from the diode row to the electronic processing circuit.

In this manner it is not only possible to recognise and indicate contamination and oil spots as points of reduced diffuse reflection (remission), on the contrary it is also possible through the shallow observing angle to recognise faults which project upwardly above the material surface, such as naps, burls or loose threads, as local shadow creating elements.

In a first embodiment the line is an inspection line which lies substantially at the center of the strip of light.

In a second embodiment the line is the shadow edge of the light strip disposed towards the row camera.

In order to change and optimise the sensitivity of the apparatus in recognising faults which project above the web surface a preferred embodiment is characterized in that the row camera is adjustable between the inspection line imaging position and the shadow edge imaging position. A particularly preferred embodiment makes it possible to select intermediate positions between the inspection line imaging position and the shadow edge imaging position.

An embodiment which makes it possible to recognise and register all web faults which can be found in transmission is characterized in that the light receiving means includes a further row camera having a diode row as a photoreceiving arrangement, with the row camera receiving light which has passed through the material web from a line illuminated by the strip of light, in particular from the inspection line, and imaging the line onto the diode row.

These faults include above all thickened and thinner portions of the web and also the occurrence of double threads or the absence of individual threads. Holes in the web can also be recognised in this way.

In one variant of this embodiment the observing beam of the row camera observing in transmission lies immediately outside of the angular range of the imaginary beam of illumination passing through the material web.

This embodiment is particularly advantageous since here the transmission row camera is swung into the near dark field whereby true fabric density images are obtained. The investigated fabrics may however not be too dense and darkly coloured for this purpose.

A particularly compact arrangement of the light receiving means is obtained through a construction which is characterized in that the row cameras are arranged in or on a shallow housing which has a narrow wall disposed opposite to the strip of light, with the narrow wall having a light entry slit extending parallel to the strip of light, and of substantially the same length as the inspection line, and having, in a region remote from light entry slot a first deflecting mirror which extends parallel to the light entry slot, with the first deflecting mirror strip deflecting the received light to a second deflecting mirror strip arranged parallel to the first deflecting mirror strip, and with the second deflecting mirror strip being disposed closer to the light entry slot but laterally displaced from the latter and directing the received light to the row camera, which is mounted at the other end close to the first deflecting mirror strip but laterally displaced relative thereto.

With this arrangement the length of the deflecting mirror strips is expediently selected so that the first and second deflecting mirror strips are made successively shorter in accordance with the received beam which converges to the objective of the row camera.

It is particularly advantageous when the observing angle of the two row cameras relative to the tangential plane to the surface at the position of the strip of light is made adjustable by arranging the row camera on an angle adjusting device. This permits the angle to be set to an ideal value for the recognition of faults, in each case in dependence on the material investigated or the prevailing fault problems.

The illuminating means of the surface inspection apparatus of the invention is preferably constructed so that it has one or more line-like light sources arranged on a common straight line with the light sources being imaged onto the material webs by a strip-like concave mirror arranged parallel to the straight line, preferably to an imaging scale of 1:1, and forming the strip of light there. In this illuminating means the width and optionally also the length of the light source(s) is preferably defined by a slot diaphragm arranged directly in front of the light source(s), with the edges of the slot diaphram sharply delimiting the strip of light generated on the material web and thus forming two shadow edges.

Several concave mirrors and light sources with slot diaphragms may be arranged in a row behind one another in order to form a throughgoing strip of light composed of several individual light strips.

The light source and the slot diaphragm are usefully made substantially shorter than the concave mirror, and the concave mirror is made substantially shorter than the strip of light. Halogen filament lamps or high pressure sodium lamps are for example suitable as a light source.

The material web is preferably movable in a direction parallel to its plane; and the strip of light is preferably arranged transverse to the direction of movement. This design is useful for, for example, material webs which are continuously delivered from a textile machine to a take-up reel.

The material web is expediently guided at the inspection line over a shallow cylindrical portion of hardened glass, the cylinder axis of which extends parallel to the inspection line.

This arrangement is particularly advantageous since in this way one obtains a completely reliable flutter and fault-free guidance of the material web in the region of the inspection line, and on the other hand the observation of the region of the web within the strip of light in transmission is not hindered.

In accordance with the invention the concave mirror can be a cylindrical mirror which is comparatively inexpensive to manufacture and is advantageous as a result of its large aperture in the cylinder axis direction. In the direction perpendicular to the cylinder axis the concave mirror should only have an aperture angle of approximately 30° in order to achieve sharp shadow edges.

Particularly preferred remission observing angles are 10° to 30°, in particular to 15° to 25° and preferably to approximately 20°.

In order to obtain a realistic image of the state of the fabric surface while observing the web it is particularly advantageous to reproduce the image on a television monitor. This can be done with an embodiment in which a television monitor is connected to the electronic processing circuit, with the output signal of the diode row being supplied to the television monitor as a line modulation signal, and with the line frequency of the television monitor being synchronised with the scanning frequency of the diode row and its line advance with the speed of the web, such that a television picture is generated of the surface of the material web moving beneath the strip of light in accordance with the number of lines present on the television monitor, with the television picture reproducing the faults as dark locations.

With this arrangement separate monitors can be provided for remission and transmission. It is however also possible to provide a single monitor and to reproduce selectively the remission or transmission image by switching over between these two images.

Figure 2:
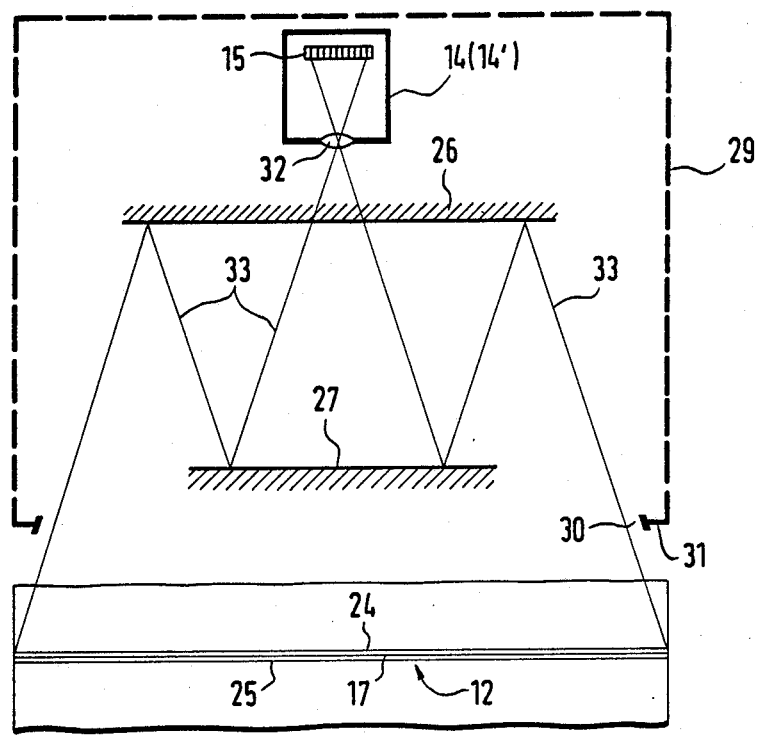
Figure 3:
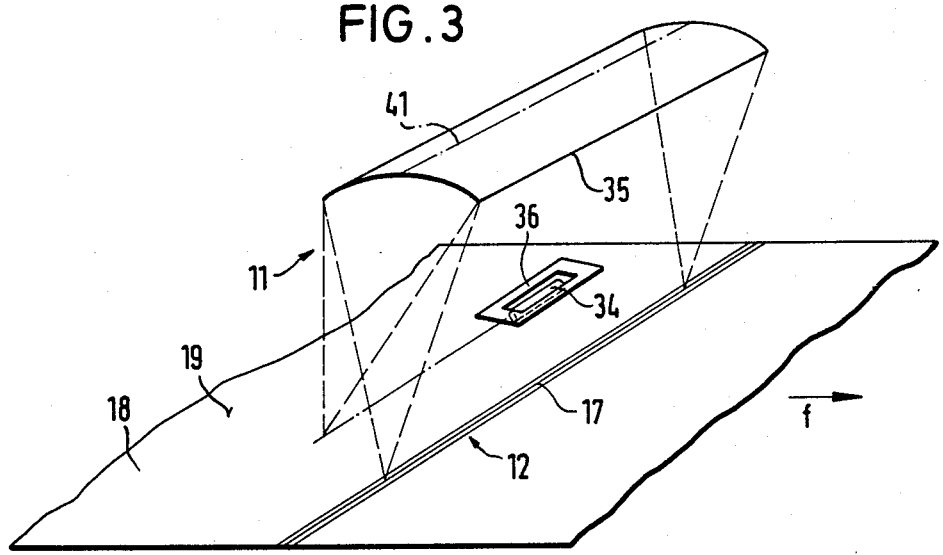
Figure 4:
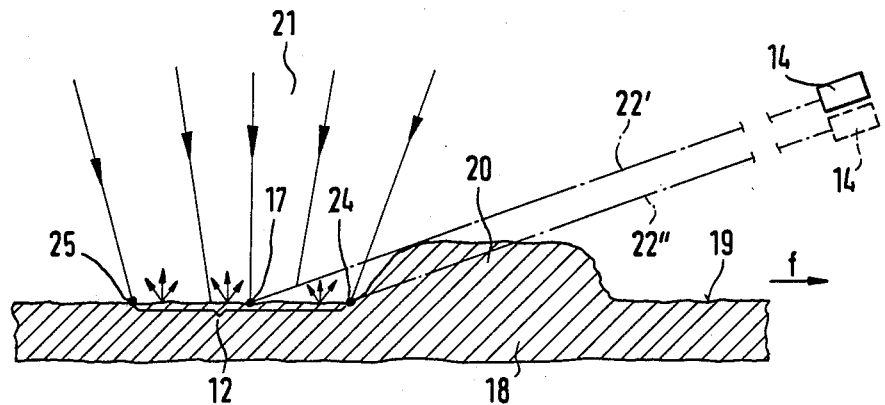

The invention will now be described in the following with reference to the drawing which shows:

FIG. 1 a schematic view of an optical surface inspection apparatus for material webs seen in the direction parallel to the planar material web and perpendicular to the direction of advance of the material web, FIG. 2 a schematic view of the light receiving means used for the subject of FIG. 1 in accordance with the lines II—II in FIG. 1, FIG. 3 a schematic perspective view of the illuminating means used for the subject of FIG. 1, and FIG. 4 a schematic enlarged sectional view of the web investigated with the surface inspection apparatus of FIGS. 1 to 3, as seen in the region of the strip of light generated on the web, in order to illustrate the fault recognition in accordance with the invention.

As seen in FIG. 1 an illuminating means 11 accommodated in a housing 40 and a light receiving means 13, which consists of two shallow housings 29 each containing a row camera 14, 14' and two deflecting mirror strips 26, 27, are connected to an angle adjustment apparatus 28. This angle adjustment apparatus 28 takes the form of two guide rings arranged alongside the two edges of the material web 18, and these guide rings are pivotable about the central axis (at 12) of the angle adjusting apparatus 28.

The material web 18 to be inspected runs diametrically between the two axially aligned guide rings of the angle adjustment device 28 in the direction of the arrow f, so that at any one time a transverse line on the surface 19 of the material web 18 coincides with the central axis (at 12) of the angle adjustment device 28.

The material web is supported from below in this region by an upwardly convexly curved transparent cylinder section 37 in order to ensure flutter-free transport in the direction f.

As seen in FIGS. 1 and 3 the illuminating means 11 comprises a straight linear light source 34 arranged directly in front of the slot of he straight slot diaphragm 36. A strip-like concave mirror 35 extends parallel to the lamp 34 and to the slot diaphragm 36 at a distance greater than its focal length. The strip-like concave mirror 35 is tilted about its central longitudinal axis (in the clockwise sense in FIG. 1) in such a way that the reflected converging light beam 21 can emerge past the light source 34 and the slot diagram 36 through a window 42 in the base of the housing 40. The representation in FIG. 3 shows the illumination means 11 in a perspective view taken obliquely from the rear in FIG. 1.

The imaging conditions in the illuminating means 11 are such that the strip-like concave mirror 35, which is preferably formed as a cylindrical mirror, images the secondary light source bounded by the edges of the opening of the slot diaphragm 36 as a narrow and sharply bounded strip of light 12 on the surface 19 of the material web 18. The longitudinal direction of the light source 34 of the slot diaphragm 36, and also of the concave mirror 35 extend perpendicular to the direction of movement f and also parallel to the material web. The material web extends flatly here, so that the strip of light which is generated extends perpendicular to the direction of advance f of the material web 18.

In accordance with FIG. 3 the light source 34 and the slot diaphragm 36 associated with it is made substantially shorter than the strip-like concave mirror 35 which in turn is shorter than the strip of light 12 which it generates. Nevertheless the strip of light 12 is also generated beyond the two ends of the concave mirror 35 since those regions of the surface 19 of the web which are located beyond the ends of the concave mirror 35 are also embraced due to the partly oblique incidence of the light emerging from the light source 34 on the concave mirror 35.

The strength of the light is however somewhat weakened there, i.e. beyond the ends of the concave mirror 35. If however one arranges several illuminating devices 11 in a row behind one another, i.e. end to end, and with a substantial spacing from the concave mirrors 35, then the illumination regions of the individual adjacent concave mirrors 35 overlap in the gaps in such a way that a substantially uniform illumination of the strip of light 12 is obtained over its entire length.

The photoelectric light receiving means 13 are each arranged, in accordance with FIGS. 1 and 2, in a shallow housing 29. A light entry slot 30 is located directly opposite to the strip of light 12 in the narrow wall 31 which extends parallel to the strip of light 12 and is preferably closed off by a window. A first deflecting strip mirror 26 is arranged at the side of the housing remote from the light entry slot 30 parallel to the light entry slot 30 and is made substantially shorter than the strip of light 12 as can be seen from FIG. 2. A further deflecting mirror strip 27 of even shorter shape is provided alongside the light entry slot 30 and deflects the light reflected from the first deflecting mirror strip 26 to the row camera 14 or 14' respectively. The length of the deflecting mirror strips 26, 27 and their arrangements are so chosen that the entire beam from the light strip 12, extending from the light strip 12 to the objective 32 of the row camera 14 or 14' respectively, is picked up. In each case a diode row 15 extending parallel to the strip of light 12 is located inside the row cameras 14, 14' and, in accordance with FIG. 1, is connected to an electronic processing circuit 16. A synchronisation signal derived from a web speed measuring device 43 is also supplied to the electronic processing circuit 16. A television monitor 38 is connected to the electronic processing circuit 16 and can be selectively controlled by a change-over switch 39 by the diode row 15 of the row camera 14 or by the diode row of the row camera 14'.

The row camera 14 is arranged above the material web 19 at an observation angle $\alpha$ of approximately 20° whereas the row camera 14' is located beneath the material web 18, and indeed angularly directly alongside the illumination beam 23 which would be generated by the illuminating means 11 in the region beneath the material web 18 if the latter were not present. The row camera 14' which operates in transmission is thus operating in the near dark field. The schematically illustrated observing beam 22 of the row camera 14' accordingly lies directly alongside the illuminating beam 23.

In so far as the illuminating means 11 illuminates the material web perpendicularly from above, as shown in FIG. 1, the diode row camera 14' or its housing 29 can preferably be arranged at an observing angle $\beta$ of approximately 15° to the vertical.

In accordance with FIGS. 1 to 3 the row cameras 14, 14' form an image on the diode rows 15 of an inspection line 17 of the web surface which is located within the strip of light 12.

FIG. 4 illustrates the manner of operation of the row camera 14 which operates in diffuse reflection. It is assumed that a light impermeable or only partially permeable fault 20 projects upwardly above the surface 19 of the material web. The inspection line 17 is to be imagined as extending perpendicular to the plane of the drawing in the same way as the shadow edges 24, 25 which bound the strip of light toward the sides. The converging illuminating beam 21 coming from the illuminating means 11 is likewise illustrated in FIG. 4. Two observing beams or observing central directions 22' or 22" are reproduced in chain-dotted lines for the schematically illustrated row camera 14 of which the one is directed onto the center of the illuminating strip 12, i.e. onto the inspection line 17 and the other 22" is directed onto the shadow edge 14 of the strip of light 12 adjacent the row camera 14 which is only shown here in broken lines.

One recognises that on adjusting the row camera 14 along the observing beam 22' the fault 20 will not be so sharply recognised as when the row camera 14 is aligned along the observing beam 22" onto the relatively sharp shadow edge 24. The fault recognition is thus substantially more sensitive with the arrangement of the row camera 14 in accordance with the observing beam 22" than when it is aligned on the inspection line 17. The desired fault detection sensitivity can be realised by changing the adjustment between the positions 22' and 22".

The manner of operation of the described inspection apparatus is as follows:

After the two row cameras 14, 14' have been set at suitable angles $\alpha$ and $\beta$ respectively to the surface of the material web 18 in the region of the strip of light 18 the illuminating means 11 and the row cameras 14, 14' are switched on while the advance of the material web 18 in the direction of the arrow f is also switched on. The electronic processing circuit 16 now receives signals from the diode rows 15 of the row cameras 14, 14' which are formed in accordance with the structure and the faults of the material web 18. These signals can be termed video signals, since they can be evaluated in corresponding manner to a video signal. The speed of advance f of the material web 18 is so selected in relation to the scanning speed of the diode rows 15 that the surface 19 of the material web 18 is scanned in gap-free manner in the transverse direction. The line jump of the television monitor 38 is so controlled by means of the synchronisation signal coming from the web speed measuring device 43, that the lines are switched on further on the television monitor 38 in accordance with the line-like scanning of the material web 18 by the diode rows 15. The amplitude of the video signal supplied to the television monitor is controlled by the output signals of the diode rows 15 so that a dark signal is generated when shadows are present caused by a fault 20, such as is shown in FIG. 4. In this manner an image of a predetermined longitudinal region of the web is formed on the television monitor 38 and runs from the top to the bottom or from the bottom to the top, and the individual faults 44 can be recognised in this image as dark locations on a bright background. It is possible to connect two television monitors 38 to the electronic evaluating circuit 16 with each of the television monitors being associated with a respective one of the row cameras 14, 14'. It is however also possible to provide a change-over switch 39 in the electronic evaluation circuit 16 which selectively permits one or other of the two row cameras 14, 14' to be connected to a single television monitor 38.

A computerwise operating fault analyser 45 can also be connected to the electronic processing circuit 16 by means of which the faults which occur can be detected classwise, and can for example be reproduced in a printout. In so doing one can use both the individual signals of the diode rows 15 of the two row cameras 14, 14' and also signals combined from the two output signals. The row cameras 14, 14' are preferably equipped with a 50 mm objective 32.

It is particularly advantageous when the two row cameras 14 or 14' and the elements 26, 27, 29 associated therewith are identically constructed.

The window 42, and optionally the window provided in the light entry slot 30 are positioned slightly inclined in accordance with the invention in order to avoid double images. The windows are mounted projecting further from the housing in order to facilitate easy cleaning. The row cameras 14, 14' are accessible for the focussing and diaphragm adjustment. For this a non-illustrated coverable housing opening is provided.

The imaging ratio of the concave mirror 35 amounts to approximately 1:1. Preferred is a slight enlargement in the ratio 1:1.5.

In a practical realisation of the described surface inspection apparatus the dimensions are as follows:

Distance object to entry window of the housing 29: ca. 30 cm

Distance entry window of the housing 29 to the objective 32: 130–140 cm

Depth of the housing 29 in the direction of the beam path: ca. 50 cm

As a result of the folded beam path one obtains in this way a reduction of the housing length to approximately ⅓rd of the length of the beam path.

Since no mirror wheel is necessary for the surface inspection apparatus of the invention, and since classical light sources which are completely non-dangerous for the eye can be used in place of a laser, the mounting of the apparatus on a goods' viewing table for visual inspection is also possible. In this way the training of the inspector or the adjustment of the automatic inspection system is made easier.

We claim:

1. Optical surface inspection apparatus for material webs the apparatus comprising an illuminating means for generating a strip of light on the surface of the material web to be inspected and a photoelectric light receiving means which receives the light remitted or diffusely reflected from the surface region illuminated by the strip of light and which directs it to a photoreceiving arrangement, with the photoreceiving arrangement delivering a signal representative of web faults to an electronic processing circuit, characterized in that the light receiving device (13) includes at least one row camera (14) having a diode row (15) and serving as a photoreceiving arrangement, with the row camera (14) receiving remitted light from a line on the surface which is illuminated by the light strip (12) and forming an image of the line on the diode row (15) and with the row camera also being arranged at such a shallow observing angle α to the tangential plane to the surface at the location of the light strip (12) that faults (20) of low height which project out of the surface (19) of the material web (18) appear to the row camera (14) as a shadow outline against the bright background of the light strip (12), so that a corresponding electrical signal is transmitted from the diode row (15) to the electronic processing circuit (16).

2. Apparatus in accordance with claim 1, characterized in that the line is an inspection line (17) which lies substantially at the center of the strip of light (12).

3. Apparatus in accordance with claim 1, characterized in that the line is the shadow edge (24) of the light strip disposed towards the row camera (14).

4. Apparatus in accordance with claim 2, characterized in that the row camera (14) is adjustable between the inspection line imaging position (22') and the shadow edge imaging position (22").

5. Apparatus in accordance with claim 4, characterized in that intermediate positions between the inspection line imaging position and the shadow edge imaging position can also be selected.

6. Apparatus in accordance with claim 1, wherein the light receiving means also receives light transmitted by the surface region illuminated by the strip of light, characterized in that the light receiving means includes a further row camera (14') having a diode row (15) as a photoreceiving arrangement, with the row camera (14') receiving light which has passed through the material web (18) from a line illuminated by the strip of light (12), in particular from the inspection line (17), and imaging the line onto the diode row (15).

7. Apparatus in accordance with claim 6, characterized in that the observing beam (22) of the row camera (14') observing in transmission lies immediately outside of the angular range of the imaginary beam of illumination (23) passing through the material web (18).

8. Apparatus in accordance with claim 1, characterized in that the row cameras (14, 14') are arranged in or on a shallow housing (29) which has a narrow wall (31) disposed opposite to the strip of light (12), with the narrow wall (31) having a light entry slit (30) extending parallel to the strip of light, and of substantially the same length as the inspection line (17) and having, in a region remote from light entry slot (30) a first deflecting mirror (26) which extends parallel to the light entry slot, with the first deflecting mirror strip (26) deflecting the received light to a second deflecting mirror strip (27) arranged parallel to the first deflecting mirror strip and with the second deflecting mirror strip (27) being disposed closer to the light entry slot (30) but laterally displaced from the latter and directing the received light to the row camera (14, 14'), which is mounted at the other end close to the first deflecting mirror strip (26) but laterally displaced relative thereto.

9. Apparatus in accordance with claim 8, characterized in that the first and second deflecting mirror strips (26, 27) are made successively shorter in accordance with the received beam (33) which converges to the objective (32) of the row camera (14, 14').

10. Apparatus in accordance with claim 1, characterized in that the observing angle ($\alpha,\beta$) of the row camera (14, 14') relative to the tangential plane to the surface (19) at the position of the strip of light (12) is adjustable b arranging the row camera (14, 14') on an angle adjusting device (28).

11. Apparatus in accordance with claim 1, characterized in that the illuminating means (11) has one or more line-like light sources (34) arranged on a common straight line with the light sources being imaged onto the material webs (18) by a strip-like concave mirror (35) arranged parallel to the straight line, preferably to an imaging scale of 1:1 and forming the strip of light (12) there.

12. Apparatus in accordance with claim 11, characterized in that the width and optionally also the length of the light source(s) (34) is defined by a slot diaphragm (36) arranged directly in front of the light source(s) with the edges of the slot diaphragm sharply delimiting the strip of light (12) generated on the material web (18) and thus forming two shadow edges (24, 25).

13. Apparatus in accordance with claim 11, characterized in that several concave mirrors (35) and light sources (34) with slot diaphragms (36) are arranged in a row behind one another in order to form a throughgoing strip of light composed of several individual light strips.

14. Apparatus in accordance with claim 11, characterized in that the light source and the slot diaphragm (36) are made substantially shorter than the concave mirror (35), and in that the concave mirror (35) is made substantially shorter than the strip of light (12).

15. Apparatus in accordance with claim 1, characterized in that the material web (18) is movable in a direction parallel to its plane; and in that the strip of light (12) is arranged transverse to the direction of movement.

16. Apparatus in accordance with claim 1, characterized in that the material web (18) is guided at the inspection line (17) over a shallow cylindrical portion (37) of hardened glass, the cylinder axis of which extends parallel to the inspection line (17).

17. Apparatus in accordance with claim 1, characterized in that the concave mirror is a cylindrical mirror (35), the cross-section of which is preferably partly cylindrical (right-cylindrical) or partly elliptical.

18. Apparatus in accordance with claim 1, characterized in that the shallow observing angle ($\alpha$) of the row camera (14) operating in diffuse reflection amounts to 10° to 30°, in particular to 15° to 25° and preferably to approximately 20°.

19. Apparatus in accordance with claim 1, characterized in that a television monitor (38) is connected to the electronic processing circuit (16), with the output signal of the diode row being supplied to the television monitor as a line modulation signal, and with the line frequency of the television monitor being synchronised with the scanning frequency of the diode row (15) and its line advance with the speed of the web, such that a television picture is generated of the surface (19) of the material web moving beneath the strip of light (12) in accordance with the number of lines present on the television monitor (38), with the television picture reproducing the faults as dark locations.

* * * * *